(12) United States Patent
Ou Yang et al.

(10) Patent No.: US 10,753,803 B2
(45) Date of Patent: Aug. 25, 2020

(54) WEARABLE BODY TEMPERATURE MONITORING DEVICE AND METHOD THEREOF

(71) Applicant: AVITA CORPORATION, New Taipei (TW)

(72) Inventors: Hsing Ou Yang, New Taipei (TW); Hsuan Hao Shih, New Taipei (TW); Ta Chieh Yang, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 329 days.

(21) Appl. No.: 15/859,704

(22) Filed: Jan. 1, 2018

(65) Prior Publication Data
US 2018/0188114 A1 Jul. 5, 2018

(30) Foreign Application Priority Data

Dec. 30, 2016 (TW) .............................. 105144038 A

(51) Int. Cl.
*G01K 1/00* (2006.01)
*G01J 5/00* (2006.01)
(Continued)

(52) U.S. Cl.
CPC .......... *G01J 5/0025* (2013.01); *A61B 5/0008* (2013.01); *A61B 5/0075* (2013.01); *A61B 5/01* (2013.01);
(Continued)

(58) Field of Classification Search
USPC .................. 374/208, 120, 121; 600/474, 549
See application file for complete search history.

(56) References Cited

U.S. PATENT DOCUMENTS

2005/0245839 A1* 11/2005 Stivoric ............. A61B 10/0012
600/549
2007/0206655 A1* 9/2007 Haslett ..................... A61B 5/01
374/141
(Continued)

FOREIGN PATENT DOCUMENTS

CN 104395719 3/2015
CN 104833427 8/2015
(Continued)

*Primary Examiner* — Mirellys Jagan
(74) *Attorney, Agent, or Firm* — Raymond Y. Chan; David and Raymond Patent Firm

(57) ABSTRACT

The present disclosure illustrates a wearable body temperature monitoring device and a method thereof. The wearable body temperature monitoring device includes a hollow shell member and a circuit board. The hollow shell member includes a sensing surface and an outer surface opposite to each other, and the sensing surface is provided with hole. The circuit board is accommodated in the hollow shell member and includes a first side surface corresponding to the sensing surface and a second side surface corresponding to the outer surface. The circuit board is provided with a non-contact temperature sensor, a wireless transmission module, a processing unit, and a battery, and the non-contact temperature sensor is disposed at the first side surface and aligned with the hole of the sensing surface. The wearable body temperature monitoring device can respond the variation of the body temperature in real time when being attached on clothes.

8 Claims, 4 Drawing Sheets

(51) Int. Cl.
*A61B 5/01* (2006.01)
*A61B 5/00* (2006.01)
*G01J 5/02* (2006.01)
*G01J 5/04* (2006.01)
*G01J 5/08* (2006.01)

(52) U.S. Cl.
CPC ............ *A61B 5/6838* (2013.01); *G01J 5/025* (2013.01); *G01J 5/041* (2013.01); *G01J 5/0818* (2013.01); *A61B 2562/0271* (2013.01)

(56) References Cited

U.S. PATENT DOCUMENTS

| | | | | |
|---|---|---|---|---|
| 2012/0029308 | A1* | 2/2012 | Paquet | A61B 5/01 600/301 |
| 2014/0288435 | A1* | 9/2014 | Richards | A61B 5/02427 600/479 |
| 2016/0029911 | A1* | 2/2016 | Lee | A61B 5/02427 600/301 |
| 2016/0073954 | A1* | 3/2016 | Meitav | A61B 5/02055 600/324 |
| 2016/0367196 | A1 | 12/2016 | Kim et al. | |

FOREIGN PATENT DOCUMENTS

| | | |
|---|---|---|
| EP | 3040696 | 7/2016 |
| EP | 3053516 | 8/2016 |
| JP | 4176438 | 6/1992 |
| JP | 2001304959 | 10/2001 |
| JP | 2001327473 | 11/2001 |
| JP | 2004129905 | 4/2004 |
| JP | 2016140682 | 8/2016 |
| JP | 2016153978 | 8/2016 |
| TW | 529711 | 4/2003 |
| TW | 245402 | 10/2004 |

\* cited by examiner

WEARABLE BODY TEMPERATURE MONITORING DEVICE AND METHOD THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present disclosure relates to a body temperature monitoring device and method. More particularly, the present disclosure relates to a non-contact wearable body temperature monitoring device and method thereof.

Description of Related Arts

The electronic thermometer is able to quickly and accurately measure temperature of human body, so the conventional mercury thermometers are replaced by the electronic thermometers in general family. The conventional electronic thermometers can be classified into a contact-type sensing thermometer and non-contact-type sensing thermometer. For example, a handheld forehead temperature sensing device is a non-contact-type electronic thermometer. The handheld forehead temperature sensing device is able to sense the temperature of forehead when the handheld forehead temperature sensing device is spaced apart from the forehead by a short distance. However, the user must press button of the handheld forehead temperature sensing device to sense the temperature, so the handheld forehead temperature sensing device is unsuitable to continuously monitor the body temperatures of infants and young children to check whether the body temperatures of infants and young children are too high.

There is a contact-type electronic thermometer suitable to continuously monitor the body temperature of the infants and young children. The sensor of the contact-type electronic thermometer must be in direct contact with the skin or directly attached on the skin surface, so the user must open the infant's outer clothes to attach the contact-type body temperature sensor on the skin of the body of infant or young child, in order to use the contact-type electronic thermometer to monitor the body temperature of the infant or young child. However, the infant or young child may be easy to catch cold during the process of using the contact body temperature sensor.

Therefore, the present disclosure is to provide a non-contact-type wearable body temperature monitoring device and a method thereof, so that the operation of continuously monitoring the body temperature of infant or young child can be more convenient, and the infant or young child can be cared better.

SUMMARY OF THE PRESENT INVENTION

An objective of the present disclosure is to provide a body temperature monitoring device which is able to provide non-contact body temperature sensing function and wearable convenience, and a method thereof.

An objective of the present disclosure is to provide a wearable body temperature monitoring device and a method, in which use an infrared light temperature sensor in cooperation with a wave collector, to continuously monitor the body temperature.

In order to achieve the objective of the present disclosure, the present disclosure provides a wearable body temperature monitoring device. The wearable body temperature monitoring device includes a hollow shell member and a circuit board. The hollow shell member includes a sensing surface and an outer surface which both are two side surfaces opposite to each other. The sensing surface is provided with a hole. The circuit board is accommodated in the hollow shell member and includes a first side surface corresponding in position to the sensing surface and a second side surface corresponding in position to the outer surface. The circuit board also includes a non-contact temperature sensor, a wireless transmission module, a processing unit, and a battery. The non-contact temperature sensor is disposed at the first side surface and aligned with the hole of the sensing surface.

Preferably, the wearable body temperature monitoring device of the present disclosure further includes a wave collector comprising a trumpet-shaped opening, and the wave collector is covered on the infrared light temperature sensor, to align with the hole of the sensing surface.

Preferably, the wearable body temperature monitoring device of the present disclosure further includes an indicator light disposed at the second side surface and exposed out of the outer surface of the hollow shell member.

In order to achieve the objective of the present disclosure, the present disclosure further provides a wearable body temperature monitoring method including steps of: providing a hollow shell member which includes a sensing surface and an outer surface which both are two side surfaces opposite to each other, wherein the sensing surface is provided with a hole; and, providing a circuit board accommodated in the hollow shell member, wherein the circuit board comprises a first side surface corresponding in position to the sensing surface and a second side surface corresponding in position to the outer surface, and the circuit board comprises a non-contact temperature sensor, a wireless transmission module, a processing unit, and a battery, and the non-contact temperature sensor is located at the first side surface and aligned with the hole.

Preferably, the method further includes a step of providing a wave collector including a trumpet-shaped opening, wherein the wave collector is covered on the infrared light temperature sensor to align with the hole of the sensing surface.

Preferably, the method further includes a step of: providing an indicator light disposed at the second side surface and exposed out of the outer surface of the hollow shell member.

According to the wearable body temperature monitoring device and the method of the present disclosure, the user can continuously monitor the body temperature of infant or young child without attaching the temperature sensor on the skin of the infant or young child, thereby improving the convenience in operation and usage of the temperature sensor.

BRIEF DESCRIPTION OF THE DRAWINGS

The structure, operating principle and effects of the present disclosure will be described in detail by way of various embodiments which are illustrated in the accompanying drawings.

DETAILED DESCRIPTION OF THE PREFERRED EMBODIMENT

Figure 1:
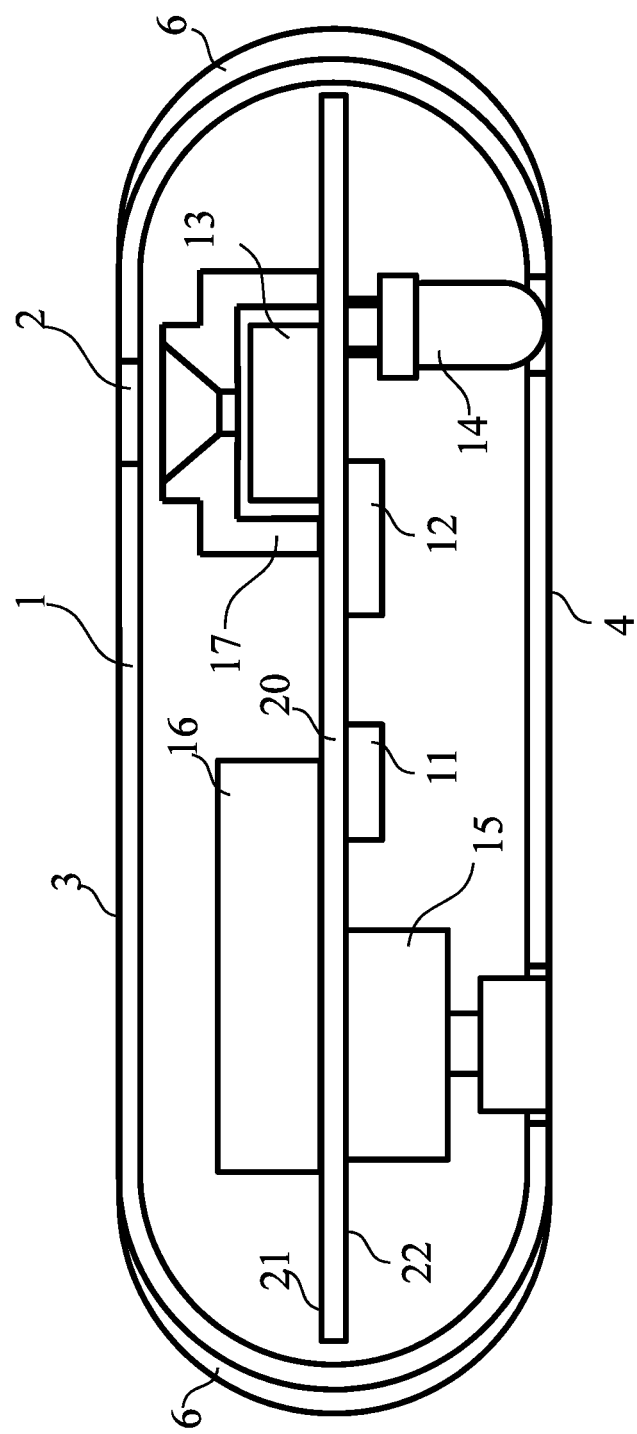
FIG. 1 is a sectional view of a wearable body temperature monitoring device of the present disclosure.

The following embodiments of the present disclosure are herein described in detail with reference to the accompanying drawings. These drawings show specific examples of the embodiments of the present disclosure. It is to be understood that these embodiments are exemplary implementations and are not to be construed as limiting the scope of the present disclosure in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

Please refer to FIG. 1. FIG. 1 shows a sectional view of a wearable body temperature monitoring device of the present disclosure. The wearable body temperature monitoring device includes a hollow shell member 1 and a circuit board 20. Preferably, the hollow shell member 1 is in a flat elliptic shape and includes a sensing surface 3 and an outer surface 4 formed on two opposite sides thereof. The sensing surface 3 includes an hole 2. The sensing surface 3 is not limited to be a plane, the elliptic shape of the shell member 1 is able to appear aesthetically appealing and fashionable; alternatively, the sensing surface 3 can be designed to have a slightly-concave radian, so that the shape of the shell member 1 can match a curve of the user's chest, thereby improving the user's comfort. Furthermore, a soft member 6 can be disposed on an elliptic perimeter between the sensing surface 3 and the outer surface 4 of the shell member 1 and served as an outer periphery part of the shell member 1, so as to increase the comfortability for the user to take and use the wearable body temperature monitoring device of the present disclosure. Alternatively, the soft member 6 can be extended to the sensing surface 3 to increase the comfortability of the sensing surface 3 in contact with the skin, but the soft member 6 must avoid the hole 2 of the sensing surface 3 from affecting the body temperature monitoring effect of the device.

In an embodiment of the present disclosure, the circuit board 20 is accommodated inside the hollow shell member 1, and includes a first side surface 21 disposed correspondingly in position to the sensing surface 3 and a second side surface 22 disposed correspondingly in position to the outer surface 4. The circuit board 20 is provided with a non-contact temperature sensor 13, a wireless transmission module 11, a processing unit 12, an indicator light 14, a power switch 15, and a battery 16 disposed on two side surfaces 21 and 22, respectively. Preferably, the non-contact temperature sensor 13 is disposed on the first side surface 21 of the circuit board 20 and aligned with the hole 2 of the sensing surface 3. Preferably, the non-contact temperature sensor 13 is an infrared light temperature sensor. The infrared light temperature sensor is covered by the wave collector 17 first, and then aligned with the hole 2 of the sensing surface 3. Preferably, the wireless transmission module 11 and the indicator light 14 are disposed on the second side surface 22 of the circuit board 20, so that, through the indicator light 14 on the outer surface 4 of the shell member 1, the user can easily observe variation of light color of the indicator light 14 which responds the monitored body temperature. The power switch 15 can be disposed on the first side surface 21 or the second side surface 22 of the circuit board 20, so as to facilitate the user to press the power switch 15 through the sensing surface 3 or the outer surface press of the shell member 1. In different embodiment of the present disclosure, the power switch 15 and the indicator light 14 both can be implemented by a switch device having the indicator light, so that the switch device can be served as the power switch of the wearable body temperature monitoring device of the present disclosure and show the variation of the light color corresponding to the monitored body temperature. In order to use the wearable body temperature monitoring device of the present disclosure, the user can power on the wearable body temperature monitoring device first, and place the wearable body temperature monitoring device in the pocket of clothes on the to-sensed-body or mount the wearable body temperature monitoring device on a necklace which is worn on the chest, and make the sensing surface 3 face toward the to-be-sensed body, thereby continuously monitoring the variation of the body temperature of the user's body.

Figure 2:
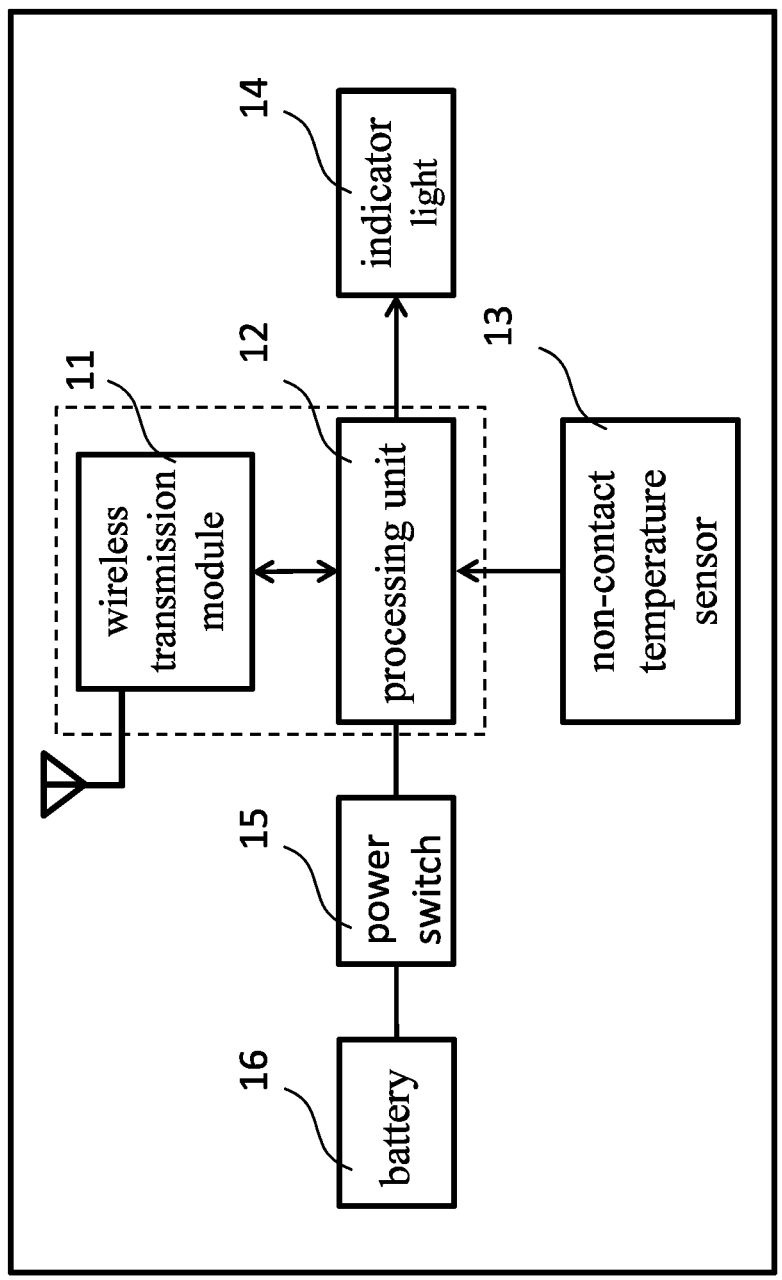
FIG. 2 is a block diagram of a wearable body temperature monitoring device of the present disclosure.

FIG. 2 shows a block diagram of the circuit board 20 of the wearable body temperature monitoring device of the present disclosure. The detail of the circuit board 20 will be described in following content.

According to the embodiment of the present disclosure, the battery 16 supplies power to the wearable body temperature monitoring device of the present disclosure. The switch 15 is disposed in an electric loop between the processing unit 12 and the battery 16, and configured to control the power supply of the battery 16 to the processing unit 12, and the battery 16 then provides power to the wireless transmission module 11, the non-contact temperature sensor 13 and the indicator light 14 through the processing unit 12. When the switch 15 controls the battery 16 to supply power to the processing unit 12, the processing unit 12 controls the indicator light 14 to light, so as to indicate that the wearable body temperature monitoring device of the present disclosure is powered on and starts to supply power to the non-contact temperature sensor 13. The indicator light 14 can emit light with various colors, and the processing unit 12 controls the variation in color of the light emitted from the indicator light 14, so as to respond the monitored body temperature. When the processing unit 12 is supplied with power, the processing unit 12 enters a temperature monitoring mode to receive a sensing signal from the non-contact temperature sensor 13 and calculate a temperature sensing value, and then determine the light color of the indicator light 14 according to the temperature sensing value. In detail, the processing unit 12 converts the sensing signal into a physical temperature first, and then converts the physical temperature into a human body's temperature according to a conversion formula established based on clinical experiment data. Furthermore, the processing unit 12 recalculates the temperature sensing value every time interval, so that the user can know the variation of the body temperature of the to-be-sensed body according to the variation of the light color of the indicator light 14 continuously corresponding to the variation of the temperature sensing value. The time interval can be a preset fixed time period.

In another embodiment of the present disclosure, the switch 15 can be a three-stage device having a power off stage, a power on stage and a wireless transmission stage. When the switch 15 is switched to the power on stage, the processing unit 12 is supplied power to execute the temperature monitoring mode, and the light color of the indicator light 14 can indicate the variation of the body temperature of the to-be-sensed body. When the switch 15 is switched to the wireless transmission stage, the processing unit 12 enables the wireless transmission module 11 to establish wireless communication with a mobile communication device (not shown in figures) through the wireless transmission module 11, so as to transmit the calculated temperature sensing value to the mobile communication device. Furthermore, the mobile communication device can execute an application program to wirelessly communicate with the device of the present disclosure.

In this embodiment of the present disclosure, the processing unit 12 and the wireless transmission module 11 can be implemented by integrated-circuit components, respectively. Preferably, the wireless transmission module 11 can be a Bluetooth wireless communication module, so that the wearable body temperature monitoring device of the present disclosure can wirelessly communicate with a smartphone or a tablet computer having Bluetooth wireless communication function, and the smartphone or the tablet computer can display the variation of the body temperature of the to-be-sensed body or output a warning message indicative of high temperature. Preferably, the processing unit 12 can be a microcontroller (MCU) including a memory configured to store a program instruction set. The microcontroller can execute the program instruction set to implement the functions of monitoring the temperature, controlling variation of light color of the indicator light 14, and controlling the wireless communication between the wireless transmission module 11 and the mobile communication device (not shown in figures). Furthermore, the mobile communication device can execute the application program to set the data stored in the wearable body temperature monitoring device of the present disclosure; for example, the mobile communication device can set the time interval by which the processing unit 12 recalculates the temperature sensing value, so as to change the response frequency of the mobile communication device or the indicator light 14 for the variation of the to-be-sensed body's temperature; alternatively, the mobile communication device can remotely set the switching operation of the device of the present disclosure. In different embodiment of the present disclosure, the processing unit 12 and the wireless transmission module 11 can be packaged integrally as a single integrated-circuit component, such as the dashed line block shown in FIG. 2; for example, the dashed line block can indicate a CPU having the wireless transmission function.

Figure 3:
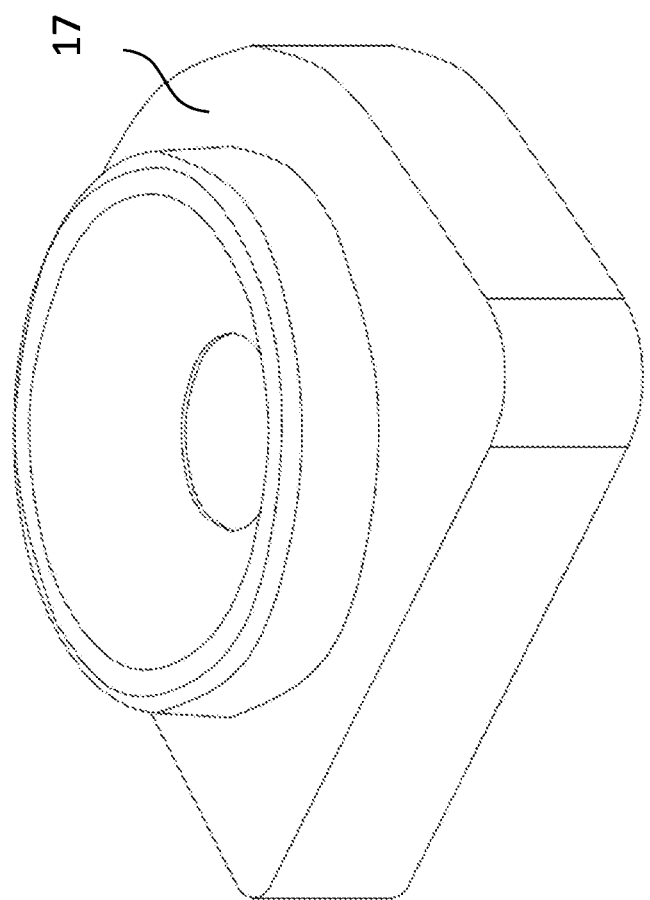
FIG. 3 is a perspective view of a wave collector of the present disclosure.

Please refer to FIG. 3. FIG. 3 shows the perspective view of the wave collector used in the device of the present disclosure. The wave collector 17 includes a trumpet-shaped opening. According to an embodiment of the present disclosure, preferably, the non-contact temperature sensor 13 is an infrared light temperature sensor, and the infrared light temperature sensor can be disposed on the first side surface 21 of the circuit board 20 and covered by the wave collector 17, and the trumpet-shaped opening of the wave collector 17 is aligned with the hole 2 of the sensing surface 3. The trumpet-shaped opening of the wave collector 17 is useful to improve sensing efficiency of the infrared light temperature sensor, so that the infrared light temperature sensor of the present disclosure is able to accurately measure temperature when the wearable body temperature monitoring device of the present disclosure is spaced apart from the to-be-sensed body's skin by 2 centimeters. Preferably, the wave collector 17 is black.

Figure 4:
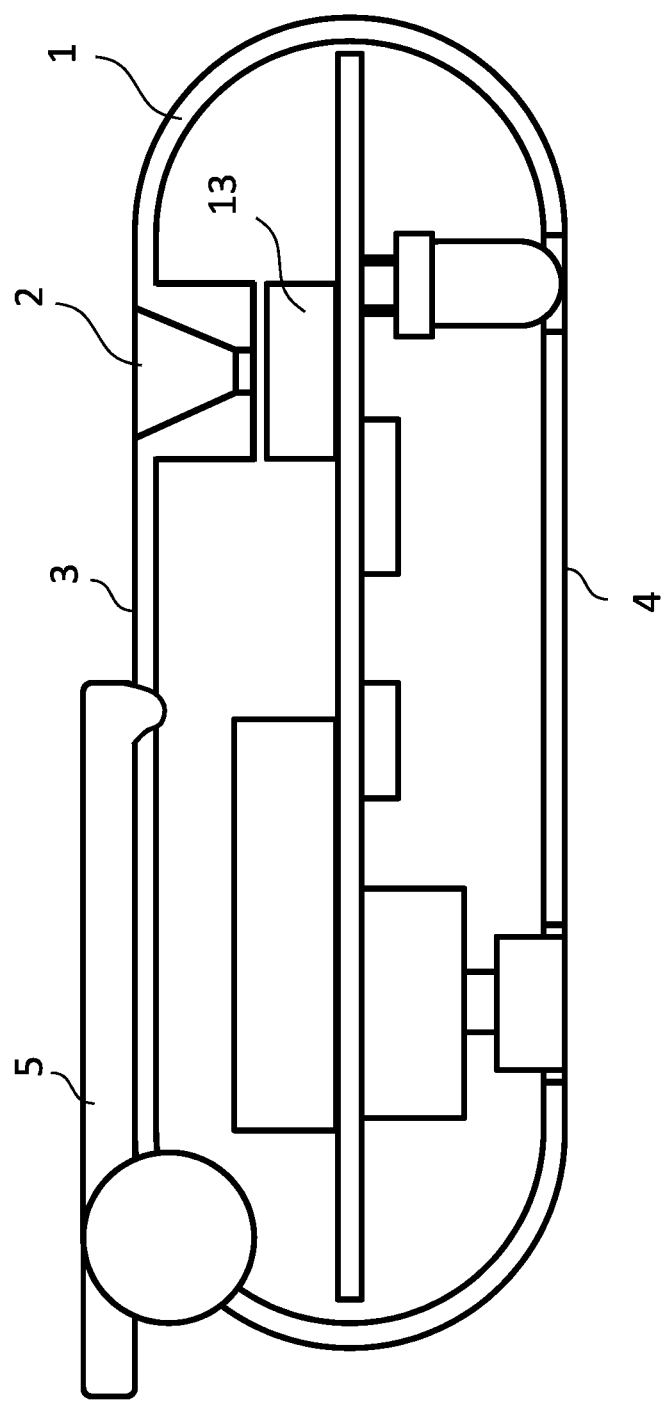
FIG. 4 is a sectional view of a wearable body temperature monitoring device provided with a clip, in accordance with the present disclosure.

Please refer to FIG. 4. FIG. 4 is a sectional view of a wearable body temperature monitoring device including a clip, in accordance with the present disclosure. The wearable body temperature monitoring device of the present disclosure can be placed in pocket of clothes on the to-be-sensed body, or mounted on the necklace which is worn on the chest, and the sensing surface 3 of the shell member 1 faces towards the to-be-sensed body. In another embodiment of the present disclosure, a clip 5 can be disposed on the sensing surface 3 of the shell member 1 and configured to clip the wearable body temperature monitoring device of the present disclosure on the clothes worn on the to-be-sensed body, and make the sensing surface 3 of the shell member 1 face towards the to-be-sensed body. Furthermore, in an embodiment of the present disclosure, the hole 2 of the sensing surface 3 of the shell member 1 can be extended inwardly by a depth to form a trumpet-shaped opening aligned with the non-contact temperature sensor 13. The trumpet-shaped opening of the hole 2 can improve the sensing efficiency of the infrared light temperature sensor.

The present disclosure disclosed herein has been described by means of specific embodiments. However, numerous modifications, variations and enhancements can be made thereto by those skilled in the art without departing from the spirit and scope of the disclosure set forth in the claims.

What is claimed is:

1. A wearable body temperature monitoring device, comprising:
    a hollow shell member comprising a sensing surface and an outer surface, wherein the sensing surface and the outer surface are two side surfaces opposite to each other, and the sensing surface is provided with a hole; and
    a circuit board accommodated in the hollow shell member and comprising a first side surface corresponding in position to the sensing surface and a second side surface corresponding in position to the outer surface, wherein the circuit board is provided with a non-contact temperature sensor, a wireless transmission module, a processing unit, and a battery, and the non-contact temperature sensor is disposed at the first side surface and aligned with the hole of the sensing surface;
    wherein the circuit board comprises an indicator light located at the second side surface and exposed out of the outer surface of the hollow shell member, and the processing unit is electrically connected to the indicator light and the non-contact temperature sensor, and configured to receive a sensing signal from the non-contact temperature sensor to calculate a temperature sensing value, and control the indicator light to emit light with different colors to indicate a variation of the temperature sensing value.

2. A wearable body temperature monitoring device, comprising:
   a hollow shell member comprising a sensing surface and an outer surface, wherein the sensing surface and the outer surface are two side surfaces opposite to each other, and the sensing surface is provided with a hole; and
   a circuit board accommodated in the hollow shell member and comprising a first side surface corresponding in position to the sensing surface and a second side surface corresponding in position to the outer surface, wherein the circuit board is provided with a non-contact temperature sensor, a wireless transmission module, a processing unit, and a battery, and the non-contact temperature sensor is disposed at the first side surface and aligned with the hole of the sensing surface;
   wherein the processing unit is electrically connected to the wireless transmission module and the non-contact temperature sensor and configured to receive a sensing signal from the non-contact temperature sensor to calculate a temperature sensing value, and control the wireless transmission module to transmit the temperature sensing value to a mobile communication device.

3. The wearable body temperature monitoring device according to claim 2, wherein the processing unit recalculates the temperature sensing value every time interval, and the time interval is set in the processing unit by the mobile communication device through the wireless transmission module.

4. A wearable body temperature monitoring method, comprising:
   providing a hollow shell member comprising a sensing surface and an outer surface, wherein the sensing surface and the outer surface are two side surfaces opposite to each other, and the sensing surface is provided with a hole;
   providing a circuit board accommodated in the hollow shell member and comprising a first side surface corresponding in position to the sensing surface and a second side surface corresponding in position to the outer surface, wherein the circuit board is provided with a non-contact temperature sensor, a wireless transmission module, a processing unit, and a battery, and the non-contact temperature sensor is located at the first side surface and aligned with the hole; and
   providing an indicator light and a power switch, wherein the indicator light is disposed at the second side surface and exposed out of the outer surface of the hollow shell member, and the power switch is disposed at the sensing surface or the outer surface of the hollow shell member.

5. A wearable body temperature monitoring method, comprising:
   providing a hollow shell member comprising a sensing surface and an outer surface, wherein the sensing surface and the outer surface are two side surfaces opposite to each other, and the sensing surface is provided with a hole;
   providing a circuit board accommodated in the hollow shell member and comprising a first side surface corresponding in position to the sensing surface and a second side surface corresponding in position to the outer surface, wherein the circuit board is provided with a non-contact temperature sensor, a wireless transmission module, a processing unit, and a battery, and the non-contact temperature sensor is located at the first side surface and aligned with the hole; and
   using the processing unit to receive a sensing signal from the non-contact temperature sensor to calculate a temperature sensing value, and control an indicator light to emit light with different colors to indicate a variation of the temperature sensing value.

6. A wearable body temperature monitoring method, comprising:
   providing a hollow shell member comprising a sensing surface and an outer surface, wherein the sensing surface and the outer surface are two side surfaces opposite to each other, and the sensing surface is provided with a hole;
   providing a circuit board accommodated in the hollow shell member and comprising a first side surface corresponding in position to the sensing surface and a second side surface corresponding in position to the outer surface, wherein the circuit board is provided with a non-contact temperature sensor, a wireless transmission module, a processing unit, and a battery, and the non-contact temperature sensor is located at the first side surface and aligned with the hole; and
   using the processing unit to receive a sensing signal from the non-contact temperature sensor to calculate a temperature sensing value, and control the wireless transmission module to transmit the temperature sensing value to a mobile communication device.

7. The wearable body temperature monitoring method according to claim 6, further comprising:
   using the processing unit to recalculate the temperature sensing value every time interval.

8. The wearable body temperature monitoring method according to claim 7, further comprising:
   using the mobile communication device to set the time interval in the processing unit through the wireless transmission module.

* * * * *